(12) United States Patent
Koutsoudis et al.

(10) Patent No.: US 12,230,370 B2
(45) Date of Patent: Feb. 18, 2025

(54) SECURE REMOTE HEALTH DATA

(71) Applicant: MASTERCARD INTERNATIONAL INCORPORATED, Purchase, NY (US)

(72) Inventors: Andreas George Koutsoudis, London (GB); Paul Michael Musser, Grass Valley, CA (US); Alex Zerio, New York, NY (US); Tara Nathan, Sherman, CT (US); Patrick L. Killian, Cottleville, MO (US)

(73) Assignee: MASTERCARD INTERNATIONAL INCORPORATED, Purchase, NY (US)

( * ) Notice: Subject to any disclaimer, the term of this patent is extended or adjusted under 35 U.S.C. 154(b) by 626 days.

(21) Appl. No.: 17/241,892

(22) Filed: Apr. 27, 2021

(65) Prior Publication Data

US 2021/0335461 A1    Oct. 28, 2021

Related U.S. Application Data

(60) Provisional application No. 63/016,672, filed on Apr. 28, 2020.

(51) Int. Cl.
*G16H 10/60* (2018.01)
*G06F 21/32* (2013.01)
*H04L 9/32* (2006.01)

(52) U.S. Cl.
CPC ............ *G16H 10/60* (2018.01); *G06F 21/32* (2013.01); *H04L 9/3231* (2013.01); *H04L 9/3239* (2013.01)

(58) Field of Classification Search
CPC ....... G16H 10/60; G06F 21/32; H04L 9/3231; H04L 9/3239
See application file for complete search history.

(56) References Cited

U.S. PATENT DOCUMENTS

| 7,404,086 B2 | 7/2008 | Sands et al. |
| 2011/0202974 A1* | 8/2011 | Leader ............... G16H 10/60 726/28 |

(Continued)

OTHER PUBLICATIONS

International Search Report, "PCT application No. PCT/US2021/029057", mailed date Jul. 22, 2021, 9 pages.

*Primary Examiner* — Jonathan Ng
*Assistant Examiner* — Benjamin L. Hanks
(74) *Attorney, Agent, or Firm* — Pillsbury Winthrop Shaw Pittman LLP

(57) ABSTRACT

The disclosure relates to methods and systems of providing secure remote health data routing for diagnostics, treatment, monitoring, and/or other health data. The system may use an anonymized identification (ID) token that may protect privacy and ensure security. The ID token may be attached with additional data such as electronic medical record (EMR) data. As such, the system may digitize and securely transmit EMR data to appropriate constituents. The system may apply routing rules and routing tables to identify the appropriate constituents. The system may also route the EMR data for storage at a user's personal device, which may include a chip card or a user device. As such, the user's personal device may store an EMR based on the EMR data, including proof of health, such as vaccination, and other health data relating to the user.

19 Claims, 11 Drawing Sheets

(56) References Cited

U.S. PATENT DOCUMENTS

| | | | |
|---|---|---|---|
| 2012/0109688 A1* | 5/2012 | Yoo | G16H 40/67 |
| | | | 705/3 |
| 2018/0117446 A1* | 5/2018 | Tran | G06F 1/163 |
| 2019/0312849 A1* | 10/2019 | Khassanov | G06F 12/1408 |

* cited by examiner

SECURE REMOTE HEALTH DATA

RELATED APPLICATIONS

This application claims priority to U.S. Provisional Patent Application Ser. No. 63/016,672, filed on Apr. 28, 2020, which is incorporated herein by reference in its entirety.

BACKGROUND

Health care testing diagnostic and treatment processes are costly, slow, and limited in the ability to share results across consuming entities. Some testing, treatment and diagnostic methods require sophisticated and expensive medical devices and technicians to operate the devices and are typically housed in limited clinical settings. This traditional paradigm results in high costs for testing and often times delay in receiving results due to the requirement for individuals to travel to the dedicated clinical site. Furthermore, as with many other health records, individuals have limited access to test, treatment and diagnostic results and such records are not easily interoperable for multiple uses.

Current processes for human disease testing, treatment, diagnostics, and reporting create numerous problems associated with addressing chronic disease and in recognizing, responding to, and managing outbreaks of disease. For example, one method of collection and analysis requires individuals to travel to sites where samples are collected. Sophisticated assay and analysis equipment may be used to analyze the sample. The relatively high cost and sophistication of the sample taking and analysis equipment leads to geographic centralization and requires travel by individuals. In more affluent and/or metropolitan geographies, the travel may be across town to a clinic, doctor's office or commercial lab. In less affluent and/or more rural geographies, the travel time and distances increase significantly. In another method, individuals may travel to collection sites to provide biological samples, which are transported to a second location for analysis. This method modularizes the process and enables more collection sites. More collection sites may reduce individual travel time and still enable scale efficiencies for the sophisticated analysis equipment and processes but does not reduce the overall testing and diagnostic time since the sample must still be transported for analysis.

Regardless of the testing, treatment and diagnostic method, the current reporting construct is oriented towards health care providers and health authorities. This approach has created a void for individuals to quickly and easily obtain a persistent and useful health record. While this void is more pronounced in less affluent geographies, lack of a usable personal record also causes problems in epidemics and pandemics where proof of immunity or vaccination is required for public-facing jobs and interactions. Furthermore, current testing and diagnostic methods are slow, costly, and may create siloed data structures with a lack of interoperability between various providers, leading to less than ubiquitous coverage and responsiveness for both chronic and disease outbreaks. The lack of, or delay in, testing, treatment and diagnostics capabilities during a disease outbreak leads to low levels of outbreak intelligence, which is a major barrier for health authorities to quickly and effectively develop disease containment and mitigation strategies. Furthermore, siloed data may result in a break in the continuity of care for healthcare treatment and adherence to care plans. In addition, the relative lack of diagnostic use in developing and other markets may lead to greater instances and impacts of disease. New assay processes via treated collection devices speeds test to analysis output, but the need to stock and re-stock pretreated collection devices increases the overall preparation time before testing can begin.

BRIEF DESCRIPTION OF THE DRAWINGS

Features of the present disclosure may be illustrated by way of example and not limited in the following figure(s), in which like numerals indicate like elements, in which.

DETAILED DESCRIPTION

The disclosure relates to methods and systems of providing secure remote health data through a trusted health data interchange network. For example, the trusted health data interchange network may store and route electronic medical record ("EMR") data of a user to health entities based on routing rules and tables that specify recipients that are registered to use the system. EMR data may refer to information relating to the health of the user stored in electronic form. An EMR may refer to a set of EMR data of the user. EMR data may include, without limitation, user identifying information, which may be anonymized and/or encrypted, assay data, diagnostic results, vaccination confirmations, health conditions, medications taken or being taken, blood type, and/or other data relating to the health of the user. In some examples, the health data interchange network may use an anonymized identification (ID) token that protects privacy and ensures security of the EMR data.

In some examples, the system may route EMR data to various recipients, including various constituents, onboarded (registered to use) to the system. In some examples, the system may route the EMR data for storage at a personal device of a user, such as a chip card or a user device. In these examples, the user's personal device may store an EMR of the user. The user may access the EMR from the personal device and/or provide a portion or all of the EMR to recipients such as entities that require proof of health (such as vaccination confirmation) for entry, first responders, health care professionals, and/or other entities.

Figure 1A:
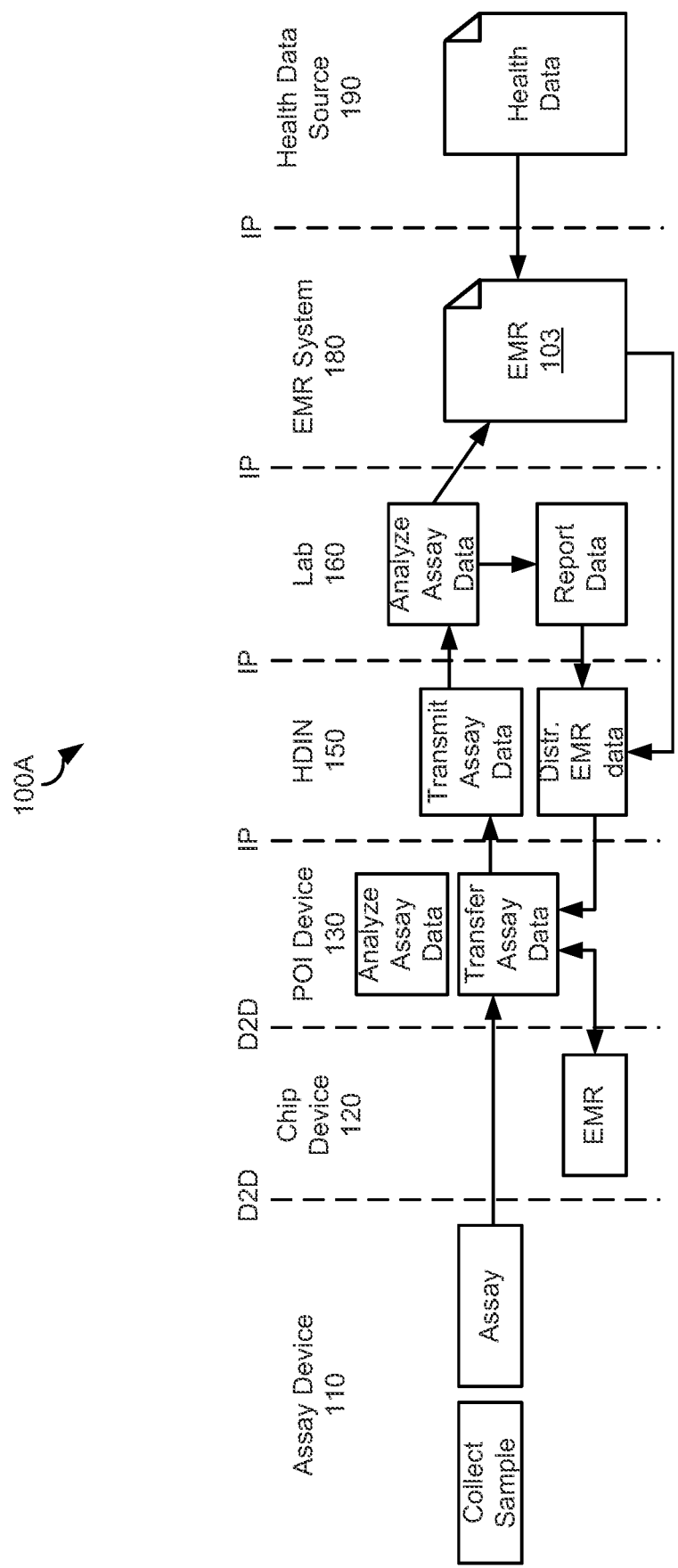
FIG. 1A illustrates an operational configuration of an example of a system of providing secure remote health data.

FIG. 1A illustrates an operational configuration 100A of an example of a system 100 (more illustrated in more detail in FIG. 1C) of providing secure remote health data. Operational configuration 100A may be suitable for markets and/or communities with low smart device penetration, while operational configuration 100B illustrated in FIG. 1B may be suitable for markets and/or communities where smart device use is widespread. It should be noted, however, that operational configurations 100A and 100B of the system 100 may co-exist within the same market as well. As such, the operational configurations 100A and 100B are shown for illustrative purposes.

Referring to operational configuration 100A, a point of interaction (POI) device 130 may be accessible by multiple users who may be each assigned with a chip device 120, which may be configured as a chip card. An assay device 110, which may integrate LoC technology, may collect biological samples and assay samples via a low-cost chip-based card form factor. After collecting and assaying the sample, the assay device 110 may transfer digital assay output via device-to-device communication, indicated by "D2D" dotted lines, to POI device 130. D2D communication may refer to data transmission directly from a sender device to a recipient device. Examples of D2D communication include a wired communication, a wireless communication such as Near-Field Communication (NFC), short-range radio such as Bluetooth™, QR encoding/decoding, and/or other communications directly from a sending device to a receiving device. The POI device 130 may analyze the digital assay output for transmission to constituents via a health data interchange network (also referred to as HDIN) 150. Alternatively, the POI device 130 may transmit the assay output via the HDIN 150 to authorized parties (over a network indicated by IP-labeled dashed lines), such as a lab 160, for analysis and reporting, in which case the POI device 130 may receive the diagnostic result from the lab 160 via the HDIN 150. In either case a diagnostic result of the assay output may be transmitted by the POI device 130 to the user's chip device 120 as an authenticated medical record. Thus, users without access to a smart device may leverage the processing capabilities of a POI device 130 and inexpensive storage and security capabilities of a chip device 120.

In some examples, a health data source 190 may generate health data and may store the health data using an EMR system 180, which stores an EMR for each patient. The EMR system 180 may transmit the EMR data to the health data interchange network 150 for storage and/or routing to recipients that have registered with the health data interchange network 150. The health data interchange network 150 may route the EMR data to appropriate recipients. In some examples, the health data interchange network 150 may route the EMR data to the POI device 130 for storage at the chip device 120.

Figure 1B:
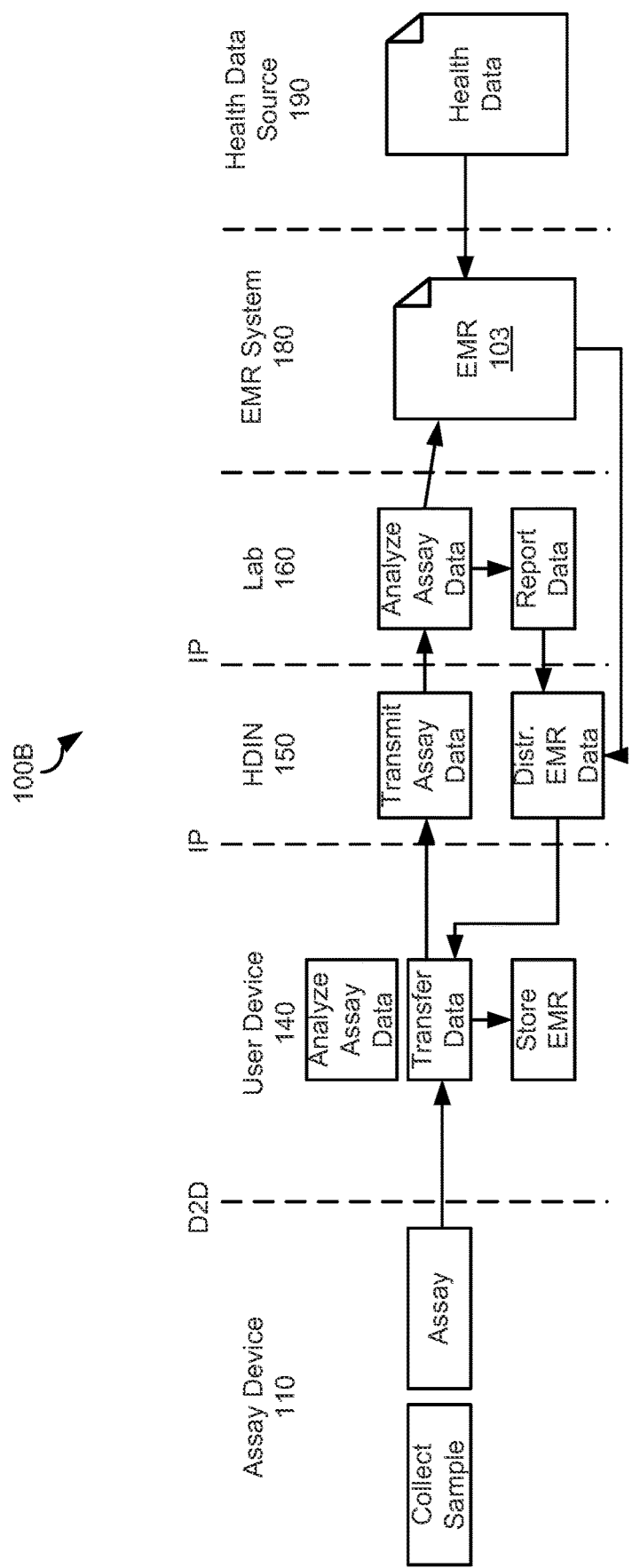
FIG. 1B illustrates an operational configuration of an example of a system of providing secure remote health data using user devices in place of point of interaction (POI) devices and chip devices.

FIG. 1B illustrates an operational configuration 100B of an example of a system 100 (more illustrated in more detail in FIG. 1C) of providing secure remote health data.

Operational configuration 100B is similar to operational configuration 100A, except that smart devices, such as a user device 140, may access the HDIN 150 instead of POI devices 130 and may directly store the diagnostic result as an authenticated medical record without the need for a chip device 120. The operational processing would be otherwise the same as operational configuration 100A.

Having described a brief description of examples of the methods and systems described herein, attention will now turn to an example of a system that facilitates secure remote health data.

Figure 1C:
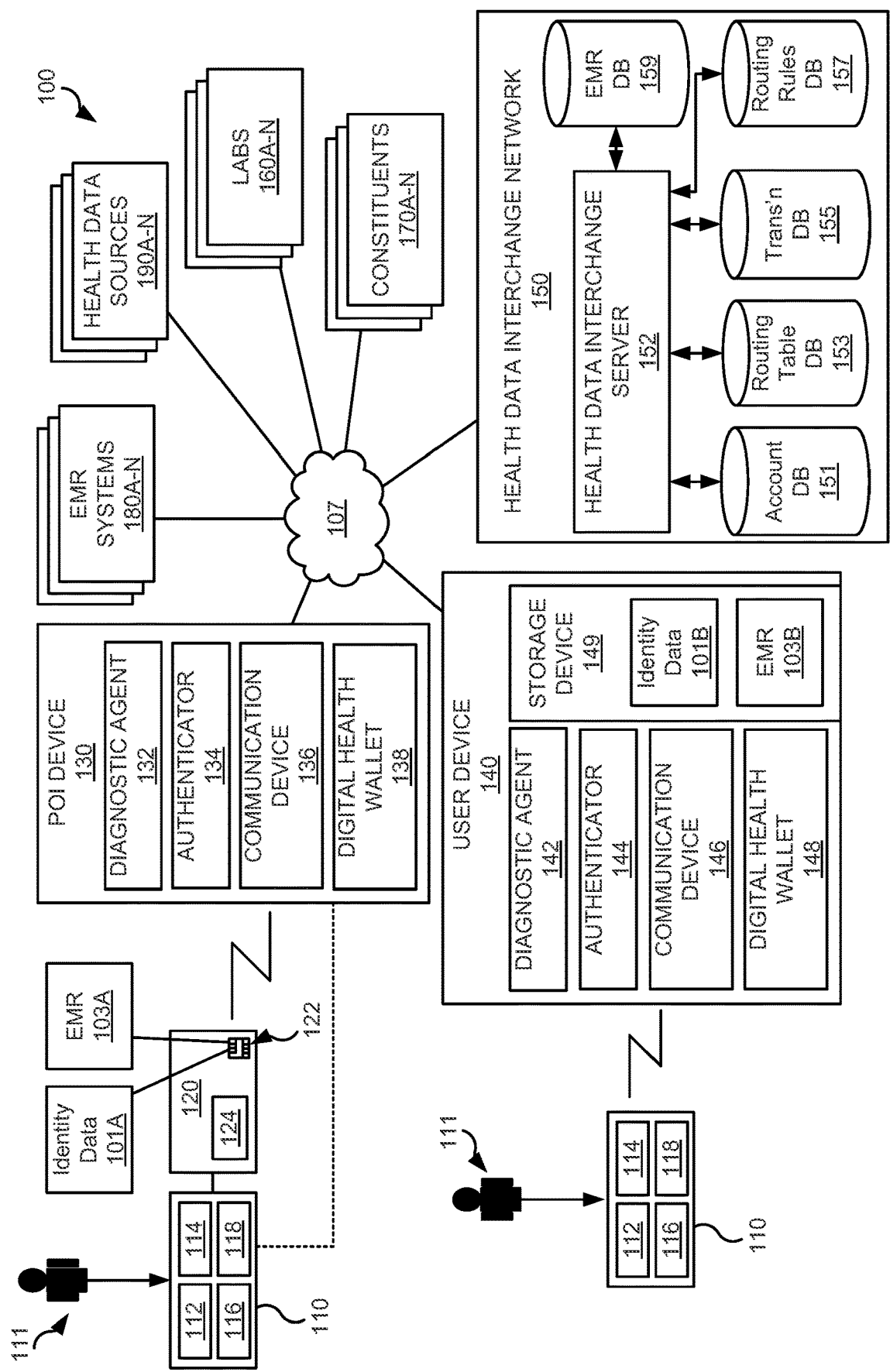
FIG. 1C illustrates an example of a system of providing secure remote health data.

FIG. 1C illustrates an example of a system 100 of providing secure remote health data. The system 100 may include an assay device 110, a chip device 120, a POI device 130, a user device 140, a health data interchange network 150, a plurality of laboratories (labs) 160A-N, a plurality of constituents 170A-N, a plurality of EMR systems 180A-N, a plurality of health data sources 190A-N, and/or other components. It should be noted that the user 111 being tested may be inferred to be a human user. However, the user 111 being assayed may include animals such as pets, farm animals, and the like.

The assay device 110 may include a sample collection system 112, an assay system 114, a communication device 116, a sleeve 118, and/or other components. The assay device 110 may refer to a device that collects a biological sample from a user 111 to conduct an on-board assay that is transmitted to a remote device for remote diagnostic analysis. In some examples, the assay device 110 may be a disposable device. The term "disposable" may refer to a limited-number use, such as a one-time use, of the assay device 110. In some examples, the assay device 110 may conduct multiple types of assays (each of which may include one or more tests). For example, a first disposable assay device 110 may include an assay for one or more first sets of conditions such as diseases, while a second disposable assay device 110 may include an assay for one or more second sets of conditions. In these examples, the assay device 110 may be associated with an identifier that identifies the assay.

In some examples, the assay device 110 may be a Micro-Electro-Mechanical Systems (MEMS) device, such as a LoC device that collects and analyses biological samples. An example of LoC technology is reported in: Wu, J., Dong, M., Rigatto, C. et al. Lab-on-chip technology for chronic disease diagnosis. npj Digital Med 1, 7 (2018), the content of which is incorporated by reference in its entirety herein.

For example, the sample collection system 112 may be configured to receive a biological sample from a user 111. The biological sample may include interstitial fluid, blood, saliva, cellular material, and/or other sample from a body of the user 111. In some examples, the sample collection system 112 may include a puncture device such as a micro-needle or nano-needle that may puncture the user 111 to obtain the biological sample. In some examples, the sample collection system 112 may include a reservoir to collect the biological sample, whether from the puncture, from a swab, an external syringe, or other source.

The sample collection system 112 may employ microfluidics to process liquid biological samples or biological samples that have been liquified. Such microfluidics may include passive microfluidics and/or active microfluidics. Passive microfluidics such as capillary, paper, or other passive forms of micro-fluid control may reduce complexity and cost. In some examples, the passive microfluidics may be aided by externally applied force such as from a centrifuge or the user 111 to aid micro-fluid control. Active microfluidics may use micro-pumps or other devices powered by an internal or external power source. Some tests performed by the assay system 114 may benefit from active microfluidics, while passive microfluidics may be sufficient for other tests. As such, the sample collection system 112 may be configured according to needs of the particular assay system 114.

Whichever type of microfluidics is used, the sample collection system 112 may direct the flow of the collected biological sample to the assay system 114. In some examples, such control may be configured (such as by designing the microfluidics to deliver) the biological sample at a certain flow rate suitable for the assay system 114.

The assay system 114 may include one or more bio-assay tests and an assay microchip. The bio-assay tests may include biochemical, chemical, and/or other agents that may interact with the biological sample to produce a test result that may be digitized by the assay microchip or otherwise formatted for transmission by the communication device 116. The digitized test result may be referred to as an assay output, which may be analysed to determine a diagnostic result. The assay output may be considered raw data produced by the assay system 114. A diagnostic result of the assay output may refer to an analysis of the assay output to determine a health condition or other state of the user 111. The health condition may include a negative diagnosis of disease, a positive diagnosis of disease, an inconclusive diagnosis, a measurement of a biological state, and/or other analysis of the assay output.

The communication device 116 may include a device that communicates the assay output to a remote device, such as the POI device 130 or the user device 140 described below. In some examples, the communication device 116 may use a device-to-device communication protocol that transfers data between two devices. The device-to-device communication protocol may be wired or wireless. In wired examples, the communication device 116 may include a plug-in device such as a dongle that may be plugged into the remote device (or vice versa) to facilitate communication between the assay device 110 and the remote device. An example of such wired device-to-device communication protocol may include a Universal Serial Bus (USB) 2.0 or USB 3.0 protocol. Other types of wired protocols may be used as well. In wireless examples, the communication device 116 may use radio communication protocols. For example, the communication device 116 may include a Near-Field Communication (NFC) antenna (or sometimes referred to as an induction loop) that may transfer an output of the assay system 114 to the remote device, such as when interrogated by the remote device. Other types of radio communication protocols such as the Bluetooth™ protocol, which may be powered by an internal or external power source.

In some examples, the sleeve 118 may include a physical retaining device to removably receive the chip device 120 for instances in which the chip device 120 and the POI device 130 are used instead of the user device 140. For example, the sleeve 118 may include retaining grooves shaped to receive the chip device 120 so that the chip device 120 may be slid in and out of the sleeve 118. Other types physical retaining devices, such as clips, straps, magnets, and/or other devices to removably retain the chip device 120 may be used.

The chip device 120 may include an embedded microchip 122, a communication device 124, and/or other components. The embedded microchip 122 may store data, which may include identity data 101A of the user 111, EMR 103A of the user 111, and/or other data. It should be noted that the identity data 101A may identify a person other than the user 111 (such as a parent of the user 111 if the user 111 is a minor or, for example, animal owner if the user 111 is an animal). However, for illustrative clarity, the identity data 101A will be described as identity data of the user 111.

The identity data 101A may include encrypted identification information that may be used to authenticate a user. The identification information may include biometric signature data (such as a fingerprint or faceprint), a secret such as a personal identification number (PIN), and/or other authentication data. The identity data 101A may include a cryptographic hash of the identification information. For example, the identity data 101A may include a one-way cryptographic hash created from the identification information using MD5, SHA-256, or other cryptographic technique that may be used by the POI device 130 or user device 140 to authenticate the user 111. As such, a user claiming to be the owner of the chip device 120 may be authenticated against the identity data 101A by obtaining identification information from that user, hashing the identification information, and comparing the hashed identification information to the identity data 101A stored on the microchip 122.

The EMR 103A may include diagnostic results of the assay output. The diagnostic results may be written to the embedded microchip 122 based on a transmission received from a remote device, such as the POI device 130, via the communication device 124. The communication device 124 may be similar to the communication device 116 of the assay device 110.

In some examples, the chip device 120 may be a multi-function identity device. In these examples, the identity data 101A may further include wallet data such as payment card information, loyalty identifiers, and/or other user-identifying information.

The POI device 130 may work in conjunction with the chip device 120 for instances in which user device 140 for each user is unavailable, such as in markets where smartphone or similar personal user devices are not widely prevalent. In these areas, chip devices 120 may be more readily available. A given POI device 130 may provide service for users that do not have access to their own user device 140. Such POI devices 130 may be placed at various locations, such as medical clinics, hospitals, retail locations, and the like. Users without user devices 140 may use assay devices 110 and have diagnostic results stored on their chip device 120. Furthermore, the POI devices 130 may be portable and therefore may not necessarily be in a fixed location.

It should be noted that the use of the chip device 120 is not necessarily limited to areas where user devices 140 are not prevalent. Rather, the chip device 120 may be used as a way to conveniently, persistently and securely store diagnostic results that are derived from assays of an assay device 110 without being stored on user devices 140, which may be changed or upgraded from time to time.

The POI device 130 may include a device such as a smartphone, a tablet device, a wearable device, a personal computer, and/or other device having computational and storage capabilities to receive assay outputs, communicate with the health data interchange server 152, and/or perform other operations described herein.

The POI device 130 may include a diagnostic agent 132, an authenticator 134, a communication device 136, a digital health wallet 138, and/or other components. The diagnostic agent 132 may include instructions, such as a mobile application, that program a processor of the POI device 130 to interrogate the assay device 110 to obtain an assay output, such by causing the communication device 136 to transmit an NFC query. In some examples, the diagnostic agent 132 may generate a diagnostic result of the assay output. In other examples, the diagnostic result may be generated by a lab 160. In these examples, the diagnostic agent 132 may transmit the assay output to the health data interchange server 152 for routing to an appropriate lab 160. For example, the diagnostic agent 132 may transmit, to the health data interchange server 152, a transaction that requests that the assay output be routed to the appropriate lab 160. Such transaction processing will be described in further detail with respect to the health data interchange network 150.

In some examples, the diagnostic agent 132 may be provided to the POI device 130 by a manufacturer (or developer acting on behalf of the manufacturer) of the assay device 110. In this manner, various manufacturers may create assay devices 110 and provide diagnostic agents 132 that may perform analysis on the assay outputs.

The authenticator 134 may include hardware and/or software to authenticate an identity of a user. In some examples, the authenticator 134 may authenticate a user based on biometric authentication such as a fingerprint, face identification, or other biometric information, a Personal Identification Number (PIN), and/or other authentication techniques that are integrated with the POI device 130. For example, the authenticator 134 may register a user by obtaining identity data (such as a biometric identification, PIN, or other identity data) of a user, hashing the identity data, and storing the hashed identity data for later comparison.

The communication device 136 may include an active NFC device that may transmit an NFC signal, such as an energizing signal, to read from NFC tags or other NFC devices. The communication device 136 may transmit other NFC signals for writing to NFC tags or other NFC devices. In some examples, the communication device 136 may include other communication devices to communicate with the assay device 110 and/or the chip device 120 as well, depending on the particular communication capabilities of those devices.

In some examples, the digital health wallet 138 may store EMR data received from various sources, such as the assay device 110, the health data interchange server 152, and/or other sources of the EMR data. In some examples, the digital health wallet 138 may be an application executed by a processor of the user device 140 to provide the POI device 130 with read, write, and transfer functionality for EMR data. For example, the digital health wallet 138 may communicate with the chip device 120, the health data interchange server 152, and/or other components to send or receive the EMR data. To receive the EMR data, the digital health wallet 138 may read encodings such as quick response (QR) codes that may encode the EMR data via an onboard imaging device (not illustrated). In other examples, the digital health wallet 138 may use the communication device 136 to receive and/or transmit EMR data via NFC or other short-range wireless communication protocol such as Bluetooth™. The term "short-range" may refer to well-defined ranges for wireless communication protocols, as would be appreciated. In yet other examples, the digital health wallet 138 may receive the EMR data via a communication network (such as communication network 107 illustrated in FIG. 1C). In some examples, the digital health wallet 138 may use the authenticator 144 to authenticate a user to ensure that only the user has access to the EMR data relating to the user.

The user device 140 may include components similar to the POI device 130 with the exception that the user device 140 may store, at storage device 149, identity data 101B and EMR 103B. The identity data 101B may be the same as the identity data 101A stored at the chip device 120, except that the identity data 101B is stored at the user device 140. Likewise, the EMR 103B may be the same as the EMR 103A stored at the chip device 120, except that the EMR 103B are stored at the user device 140. The user device 140 may include a diagnostic agent 142, similar to the diagnostic agent 132, an authenticator 144 similar to the authenticator 134, a communication device 146 similar to the communication device 136, and a digital health wallet 148 similar to the digital health wallet 138. In the user device 140, the digital health wallet 148 may include functionality to provide a health credential of the user. A health credential may refer to all or a portion of the EMR 103B of the user that may be transmitted to other devices as a proof of health. For example, the health credential may include a vaccination confirmation to facilities or countries that require vaccinations for entry, health conditions to show prior histories, allergies, or blood types, and/or other EMR data included in the EMR 103B. The transmission of the health credential may be subject to user authentication and approval to provide the health credential. The health credential may be tokenized in a secure manner, similar to the way in which the health data interchange server 152 tokenizes data as described herein.

It should be noted that the digital health wallet 148 may customize the health credential according to particular needs and/or user input. For example, the digital health wallet 148 may customize a health credential to include only a vaccination confirmation for entities that require or request proof of vaccination. In another example, the digital health wallet 148 may customize a health credential to include only a blood type, allergies, and prior medical history for provision to emergency responders.

In some examples, the digital health wallet 148 may provide the health credential directly to another device via the communication device 146. In other examples, the digital health wallet 148 may generate a QR code that encodes an identifier that identifies the user. A recipient (such as an entity requiring proof of health, a first responder, a healthcare provider, or other entity) may scan the QR code and transmit the identifier to the health data interchange server 152. The health data interchange server 152 may identify the EMR in the EMR database 159 corresponding to the identifier. In some examples, the health data interchange server 152 may transmit a request, to the user (such as via the digital health wallet 148 of the user) to confirm the provision of the health credential. Such confirmation may require authentication via the authenticator 144. In some examples, the confirmation may also require the user to identify a portion or all EMR data that should be provided. In other examples, the recipient may identify such portion or all EMR data, in which case the health data interchange server 152 may prompt the user to confirm such request.

It should be noted that chip device 120 may operate to also cause the provision of the health credential. For example, the chip device 120 may be inserted into a recipient's reader or otherwise be read by a POI device 130, which may then perform functionality similar to the digital health wallet 148 to provide or cause to be provided the health credential.

The health data interchange network 150 may include a health data interchange server 152, an account database 151, a routing table database 153, a transaction database 155, a routing rules database 157, an EMR database 159, and/or other components. The health data interchange network 150 may provide many-to-many routing and transmitting of assay and/or analysed data between the POI device 130 or user device 140, the labs 160A-N, and the constituents 170A-N. Data received by or transmitted through the health data interchange network 150 will be referred to as "interchange data."

The health data interchange server 152 may mediate the exchange of interchange data based on transactions submitted by enrolled entities. A transaction may refer to a request submitted by an enrolled entity to share, request access to, or otherwise interact with other enrolled entities through the health data interchange server 152. A transaction may provide a uniform encoding for EMR data. Thus, the health data interchange server 152 may facilitate the exchange of disparate data formats and sources used by various enrolled entities. Transactions may be routed through secure communication channels defined by the routing table database 153 by applying routing rules from the routing rules database 157.

In some examples, data of each transaction may be encrypted for transport (transmission via communication network 107) and/or storage. For example, the assay output and the diagnostic results may each be encrypted using a one-time use encryption key, and may be exposed as encrypted data. The encrypted data may include, for example, an encrypted JavaScript Object Notation (JSON) object. The contents of the JSON object string may be encrypted based on a single-use Advanced Encryption Standard (AES) key. Such encryption may use Cipher Block Chaining (CBC) (encryption in CBC mode).

The one-time use encryption key may be wrapped with a public key associated with the health data interchange server 152, in a Rivest-Shamir-Adleman (RSA) digital envelope exposed by the API. In particular examples, data from a transaction may be tokenized via JSON web token (JWT). In this example, the health data interchange server 152 may provide an Application Programming Interface (API) to tokenize data prior for transportation over the communication network 107. In particular, a sender may use the API to tokenize data from a transaction for transmission via the health data interchange server 152. For example, the POI device 130 or the user device 140, via the API of the health data interchange server 152 may tokenize the assay output for transmission to a lab 160 or for storage by the health data interchange server 152. Such tokenization may result in a JWT that may then be securely transmitted to the lab 160.

In some examples, only enrolees may submit transactions (and therefore access the interchange data). During enrollment, account identifiers may be assigned to an entity enrolling to participate in the system. For example, the account identifiers may include a chip device identifier for a user 111 assigned with a chip device 120, a user account identifier for a user 111 that uses a user device 140, a device identifier for a POI device 130 registered to use the system, a lab identifier for each lab 160 enrolled to process assay outputs, and a stakeholder identifier for each constituent 170, and/or other identifiers for entities that may use the health data interchange network 150. Each account identifier may be stored in the account database 151. Each account identifier may also be stored in association with an account type to identify the type of entity (such as user, device, lab, stakeholder, and so forth) that has been assigned with the account identifier, and/or other attribute of the enrolled entity.

Each account identifier may include an identification (ID) token that may facilitate acquisition and tracking of anonymized data elements such as geo-mapping, demographic data (e.g. age, sex, etc.), and testing or diagnostic-specific data such as immunization and/or test date, booster date, place, outcome, etc.

In some examples, privacy and security of transactions may be facilitated through the use of secure routing and account techniques employed by payment networks, such as the Mastercard® network. In some examples, the health data interchange network 150 may leverage the trust and security of the payment network to securely and privately transmit and store the EMR data such as the assay output, diagnostic results, and/or other health data described herein. In some examples, the payment network may be considered a multipurpose network that is used to not only facilitate payments through its network but also facilitate the transmission of assay outputs, diagnostic results, and/or other data described herein using its secure and private communication links and techniques. In some examples, the health data interchange network 150 may be integrated with the payment network and vice versa. Put another way, the payment network may integrate the functionality of the health data interchange network 150 in addition to processing payment transactions and vice versa. Likewise, the health data interchange server 152 may integrate the functionality of a server device in the payment network and vice versa.

For example, techniques used by the payment network to secure payment card numbers, such as credit card numbers and Personally Identifying Information (PII) may be extended to secure assay outputs, diagnostic results, and/or data described herein, including any PII of the user 111. In this sense, the transactions submitted by a sending device (such as any of the devices illustrated in FIG. 1) to transmit data via the health data interchange network 150 may be treated by the payment network as a payment transaction request for purposes of securing the data relating to the transaction. In some examples, the payment network may include a plurality of interface processors distributed at various locations. In these examples, the transactions may be transmitted to and processed by the interface processors.

In some examples, a transaction may include a message that is formatted in a manner similar to or otherwise based on International Organization for Standardization (ISO) encoding specifications for messages, such as an ISO 8583 protocol. An ISO 8583 message may encode an electronic transaction for payment card processing on the payment network. The transaction may be encoded to be recognized by the payment network but distinguished from a payment transaction. Likewise, data transmitted from the health data interchange network 150 to a recipient may be treated as secure transaction data relating to a payment on the payment network. Still likewise, data stored by the health data interchange network 150 may be treated as payment or PII data relating to a payment on the payment network. Thus, the health data interchange network 150 may leverage the secure and private transmission and processing of a payment network, such as the Mastercard® network.

In some examples, each device connected to a network may be enrolled to use the system with a network address at which the device may be reached. The network address may include an Internet Protocol or other address, which may be stored in the routing table database 153 in association with the appropriate account identifier. In these examples, entities not enrolled to use the system may not have access to the system, enhancing security of exchange of the interchange data. The routing table database 153 may specify a network address (such as an IP address), communication protocol used, and/or other data to communicate with an entity over a network. Thus, entities not enrolled with the health data interchange network 150 may not have an entry in the routing table database 153 and therefore may not have access to the data exchanged by the health data interchange network 150.

The transaction database 155 may store a record of transactions processed by the health data interchange server 152. For example, the health data interchange server 152 may assign each transaction with a transaction identifier, which may bind data and parties to the transaction. For example, when a remote device such as the POI device 130 or the user device 140 submits a transaction to route assay output to a lab 160, the health data interchange server 152 may assign a transaction identifier to the transaction. The health data interchange server 152 may store, in the transaction database 155, the transaction identifier in association with the transaction details (such as the assay output, any location information provided by the submitter, and so forth) and the submitting party, such as the device identifier of the remote device. The lab 160 may analyze the assay output, generate a diagnostic result, and respond by submitting a transaction that includes the transaction identifier and the diagnostic results. The health data interchange server 152 may store, in the transaction database 155, the diagnostic results, the entity of the submitting lab, and the diagnostic results (or pointer to where the diagnostic results are stored) in association with one another. The diagnostic results may therefore be bound to the original transaction and the response may be forwarded to the device that submitted the transaction.

The routing rules database 157 may store routing rules that specify parameters for sending or accessing the interchange data. The parameters may be used to identity parties who may send or access the interchange data. The routing rules may include assay-defined rules, user-defined rules, system-defined rules, and/or other rules.

Assay-defined rules may specify secure routing based on a type of the assay output being routed. For example, a first type of assay may be routed to a lab 160A for processing while a second type of assay may be routed to a lab 160B for processing. When a remote device, such as the POI device 130 or the user device 140) originates a transaction to transmit assay outputs for diagnostic analysis, the health data interchange server 152 may consult an appropriate assay-defined rule to identify a lab 160 that is to receive the transaction for processing.

In another example, certain types of assays may implicate public health such as assays for detecting contagious diseases. In these instances, assay-based rules may specify that certain governmental or non-governmental health organizations may be provided with access to the assay output and/or corresponding diagnostic results.

A user-defined rule may be defined by users to control their data. For example, the user-defined rule may permit or restrict access to some or all interchange data pertaining to the user. A system-defined rule may be specified by the constituents 170A-N that may participate in the health data interchange network 150. For example, the system-defined rules may specify which entities are to access interchange data, issue account identifiers for enrolees, and/or other rules that may be agreed upon by one or more of the constituents 170A-N.

The interchange data may be stored in the EMR database 159. Such data may be anonymized to protect personal identifying information (PII), while facilitating relevant community analysis of the data. In some examples, the health data interchange server 152 may provide access to individual and/or aggregate data records in the EMR database 159. Such access may be subject to the routing rules database 157. In some examples, the access may be subject to requests from a digital health wallet 148 to provide EMR data for a health credential, as described with respect to the digital health wallet 148.

In some examples, the health data interchange server 152 may perform analytics on the interchange data stored in the EMR database 159. Such analytics may include geographic analysis of the diagnostic results (such as for transactions submitted with GPS or other location data), trend patterns, and/or other aggregations and reporting.

The plurality of laboratories (labs) 160A-N may include entities that may analyse assay outputs to generate diagnostic results. The labs 160 may enroll to participate in order to obtain access a revenue stream but also, in some examples, to develop and market assay devices 110.

The plurality of constituents 170A-N may include health system authorities and sponsors, health care providers, insurance providers, non-health care entities, individuals, and/or others. These constituents may benefit from the use of the system 100 in various ways.

The health system authorities and sponsors may include government health authorities, non-government organizations (NGO's), and Innovation Development and Operation Services (IDOs), and others who may be interested in acute and chronic disease management programs where the cost, speed, and ubiquity of testing and diagnostic programs are value drivers. For example, government health authorities may benefit from ubiquitous testing and diagnostics, which may lead to more and better information to be used in managing health care funding and managing health/disease emergencies.

NGOs may benefit from lower cost and simpler testing and diagnostic capability, which may enable NGOs to deliver higher quality and more cost-efficient outcomes. IDOs may benefit from richer data derived from broad based testing and diagnostics linked to anonymized identities, which may enable IDOs to make better funding decisions and more effectively track outcomes.

Health care providers may include entities such as physician offices, clinics, small and rural hospitals, and private labs, and other that may benefit from better, faster, cheaper testing and diagnostics in the performance of their respective care delivery roles. Physician offices may benefit from lower cost testing and faster results, which may enable physicians to deliver better, more efficient health care to patients. Private labs may benefit from lower cost testing and the ability to use unsophisticated testing sites may enable these labs to increase efficiency and grow their market coverage and associated revenues.

Clinics may benefit from lower cost per test and faster results, which may enable clinics to more and better utilize advanced testing and diagnostics to achieve positive treatment outcomes. Small and rural hospitals may benefit from reduced complexity of medical equipment and specialized personnel, which may enable small and rural hospitals to "in-source" more testing and diagnostics, reducing the dependence on, and delay associated with, remote labs. In some examples, entities that use disparate EMR systems 180 or other health data systems that are incompatible with one another may share privacy and security-compliant EMR data through the health data interchange network 150 through routing table entries, which may be approved by the user to which the EMR data relates.

Non-health care entities may include entities such as employers, public events organizers, and travel companies and others who may be consumers of event-focused testing services. Such entities may benefit from faster and lower cost testing services.

Employers may benefit because persistent health records may reduce the cost and delay of testing for positive-event credentials; while faster and less expense negative-event testing will improve the efficiency of hiring processes.

Public events organizers and travel companies may benefit from reduced risk or liability by requiring proof of immunity or immunization as a condition for entry or participation. Fast, low cost proof of health via persistent health credentials will be a valuable tool to satisfy this potential need. For example, chip card readers and other NFC readers may be able to obtain proof of health from users of the system 100.

Individuals may include those who may wish to secure "proof of health" as a credential for access to societal rights and privileges, such as to gain employment or enter public events. The ability for individuals to retain an interoperable, persistent record of immunities, immunizations, and other health states (such as confirmation of being disease-free) may reduce the cost, delay, and inconvenience of repetitive testing.

The plurality of EMR systems 180A-N may include health information and management systems that generate and store EMRs of users. For example, an EMR system 180 may include digital health tools used by healthcare providers for patient care including disease prevention, diagnosis, health management, and treatment. Alternatively, or additionally, an EMR system 180 may store assay data and/or diagnostic results of the assay data. The assay data and/or the diagnostic results may originate from labs 160, assay devices 110, and/or other sources of assay data.

The plurality of health data sources 190A-N may include sources of health data 192 that may be processed and/or stored as an EMR by the EMR systems 180. For example, a health data source 190 may include labs 160 that provide assay outputs or diagnostic results, constituents 170 that provide health data 192, and/or other entities may be provide health data 192.

The use of the system 100 may also mitigate the need for individuals to travel to specialized locations for sample collection. For example, common locations such as retail locations, clinics, and so forth may stock the assay devices 110, in effect greatly increasing the collection network. Utilizing a card form factor for the assay devices 110 and utilizing common smart devices (such as user devices 140) for analysis and/or for transmission, may reduce the need for specialized equipment and operator training thus reducing the cost per test.

Leveraging an anonymized ID token may enable richer data to be collected to support outbreak management without compromising individual privacy. Linking an individual's ID token to dynamic data sources may allow authorities to observe and track the dynamic progress of immunization and treatment programs in real time. This system may enable the individual user to retain a record of the diagnostic event for future use and proof. Stored on the individual's personal device (such as user device 140 or chip device 120) may ensure privacy, security, and control over their personal medical record.

Figure 2A:
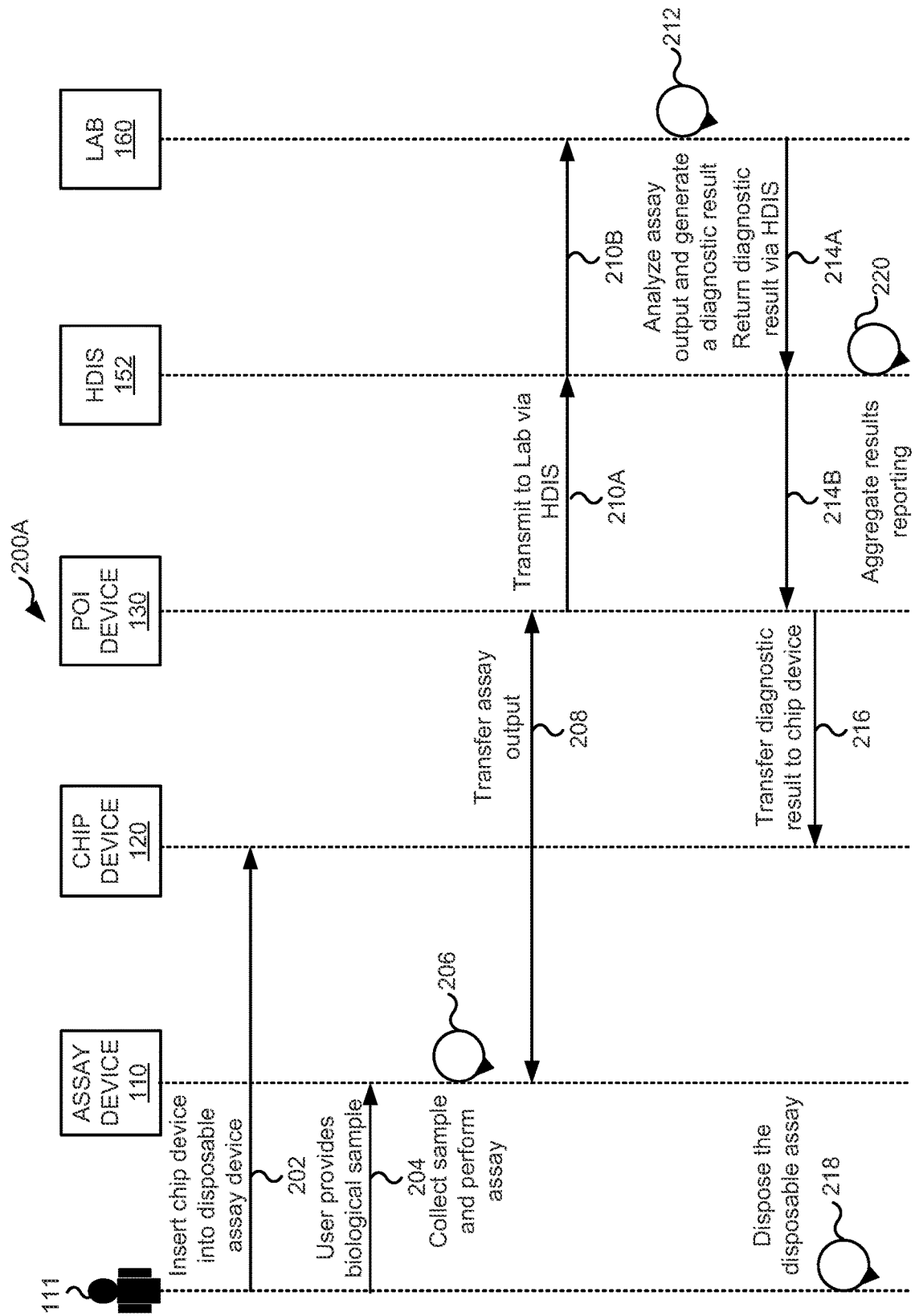
FIG. 2A illustrates a data flow diagram of using point of interaction (POI) devices in conjunction with chip devices to provide remote health data with secure routing to assay processing facilities for diagnostic processing.

FIG. 2A illustrates a data flow diagram 200A of using point of interaction (POI) devices in conjunction with chip devices 120 to provide remote health diagnostics with secure routing to assay processing facilities for diagnostic processing.

At 202, the user 111 may insert the chip device 120 into the assay device 110. If the user does not have a chip device, the user may be enrolled and assigned with a chip device.

At 204, the user 111 may provide a biological sample to the assay device 110. For example, the user may prick a finger at the collection system 112.

At 206, the assay device 110 may collect the biological sample and perform the assay system 114. For example, puncture devices such as micro-needles or nano-needles embedded in the collection system 112 of the assay device 110 may draw the biological sample to the assay system 114, which may perform one or more biological tests and convert the results in digital form on chip memory of the assay system 114 to produce the assay output.

At 208, the assay output may be transferred from the assay microchip to the POI device 130 via an NFC query originated by POI device 130. For example, the diagnostic agent 132 may initiate the NFC query and obtain the assay output from the assay device 110.

At 210A and 210B, the POI device 130 may transmit a transaction to transfer the assay output, via the health data interchange server (illustrated in FIG. 2A as HDIS) 152, to a lab 160 for processing.

At 212, the lab 160 may analyze the assay output and generate a diagnostic result.

At 214A and 214B, the lab 160 may initiates a transaction to return the diagnostic result to the POI device 130 via the health data interchange server 152.

At 216, the POI device 130 may transfer the diagnostic result to the chip device 120. Such transfer may be subject to user authentication described herein. For example, the POI device 130 may initiate an NFC write action to write the diagnostic result to the chip device 120.

At 218, the user may dispose the assay device 110 according to local instructions.

At 220, on a periodic basis, the health data interchange server 152 may perform anonymization and aggregation of testing and diagnostic results, and may generate aggregate reports for delivery to authorized constituents.

Figure 2B:
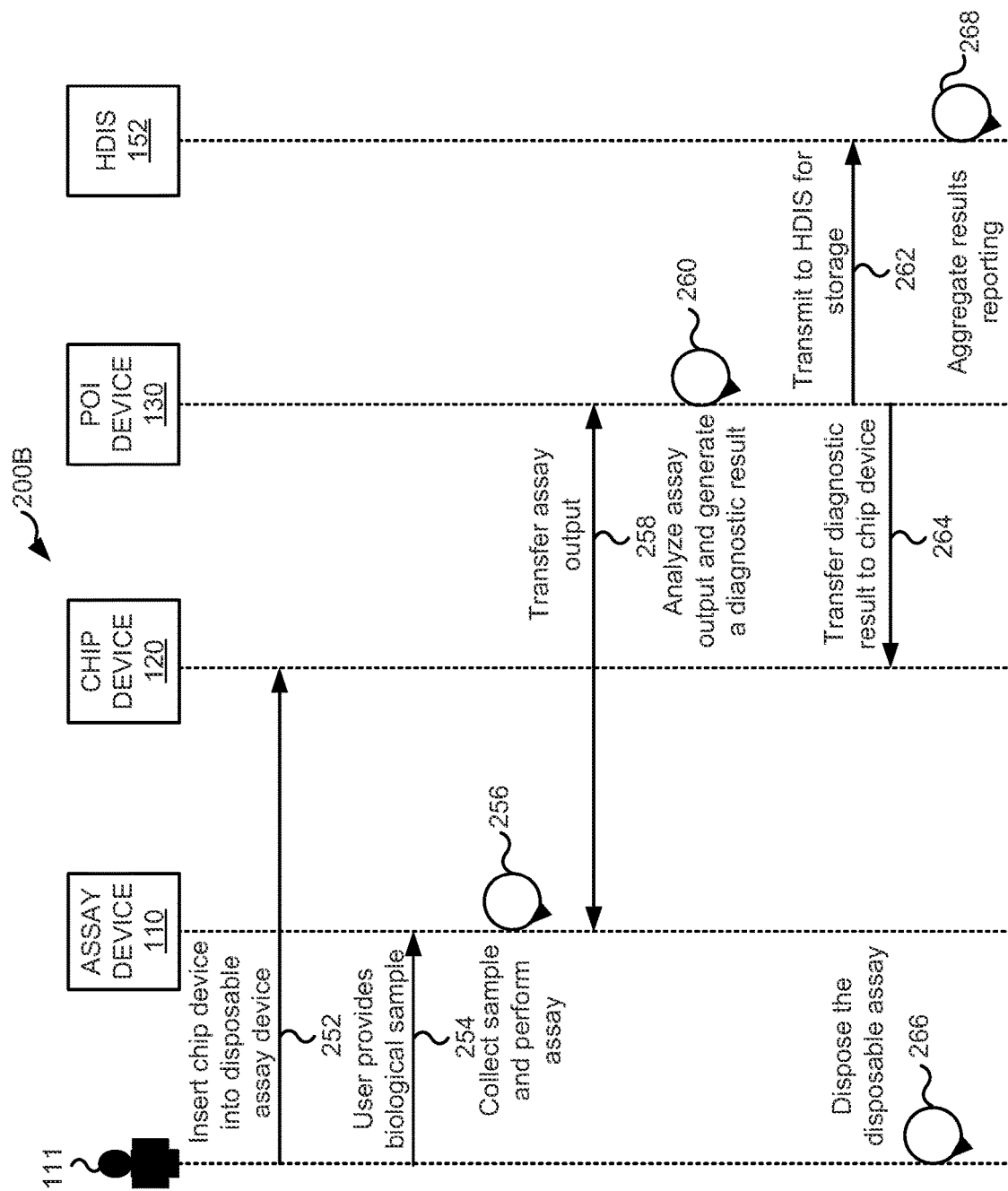
FIG. 2B illustrates a data flow diagram of using POI devices in conjunction with chip devices to provide remote health data with diagnostic processing at the POI devices.

FIG. 2B illustrates a data flow diagram 200B of using point of interaction (POI) devices in conjunction with chip devices 120 to provide remote health diagnostics with diagnostic processing at the POI devices 130.

At 252, the user 111 may insert the chip device 120 into the assay device 110. If the user does not have a chip device, the user may be enrolled and assigned with a chip device.

At 254, the user 111 may provide a biological sample to the assay device 110. For example, the user may prick a finger at the collection system 112.

At 256, the assay device 110 may collect the biological sample and perform the assay system 114. For example, puncture device such as micro-needles or nano-needles embedded in the collection system 112 of the assay device 110 may draw the biological sample to the assay system 114, which may perform one or more biological tests and convert the results in digital form on chip memory of the assay system 114 to produce the assay output.

At 258, the assay output may be transferred from the assay microchip to the POI device 130 via an NFC query originated by POI device 130. For example, the diagnostic agent 132 may initiate the NFC query and obtain the assay output from the assay device 110.

At 260, the POI device 130 (as programmed by the diagnostic agent 132) may analyze the assay output and generate a diagnostic result.

At 262, the POI device 130 may initiate a transaction to transmit the diagnostic result to the health data interchange server 152 for storage at the EMR database 159.

At 264, the POI device 130 may transfer the diagnostic result to the chip device 120. Such transfer may be subject to user authentication described herein. For example, the POI device 130 may initiate an NFC write action to write the diagnostic result to the chip device 120.

At 266, the user may dispose the assay device 110 according to local instructions.

At 268, on a periodic basis, the health data interchange server 152 may perform anonymization and aggregation of testing and diagnostic results, and may generate aggregate reports for delivery to authorized constituents.

Figure 3A:
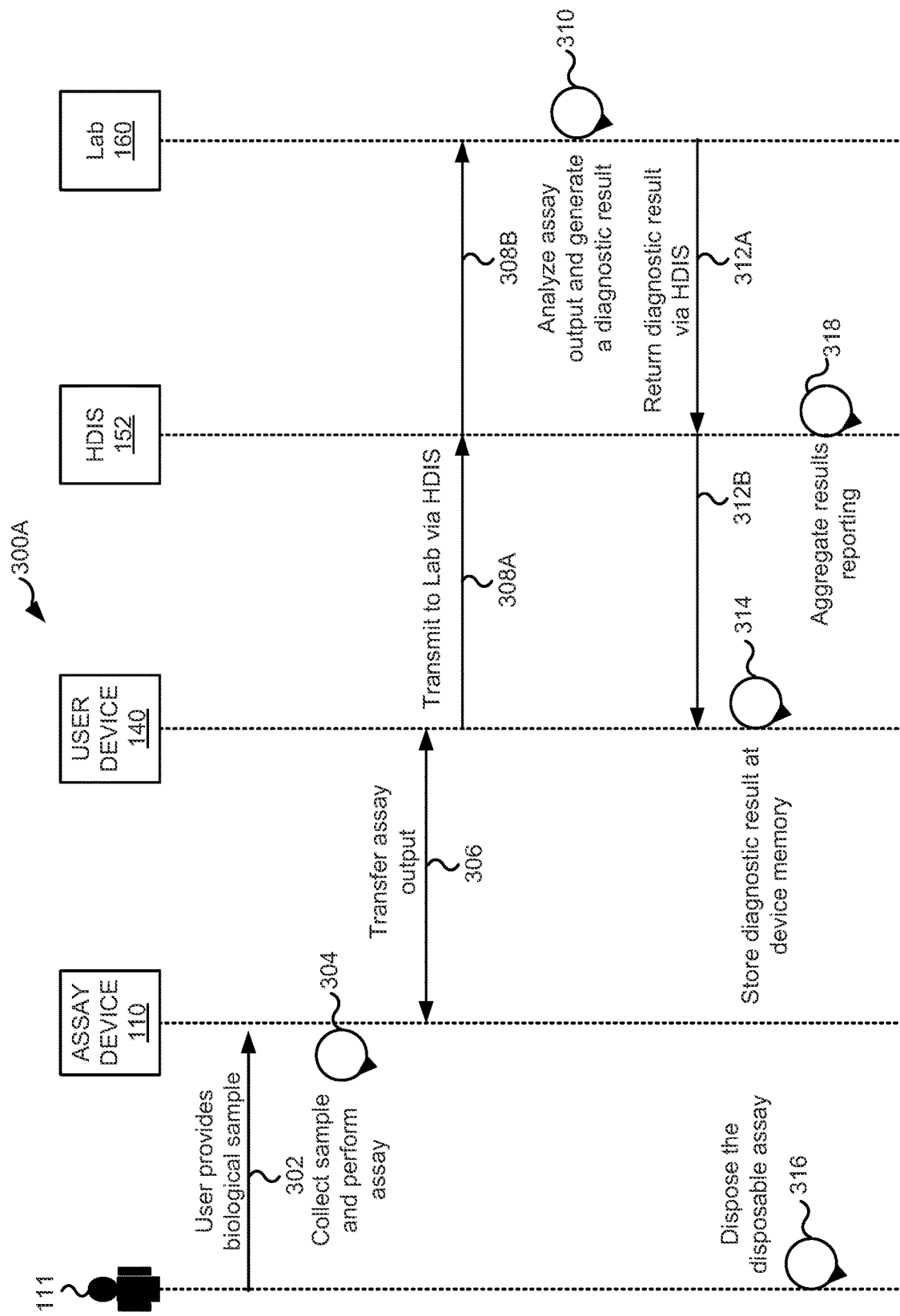
FIG. 3A illustrates a data flow diagram of using user devices to provide remote health data with secure routing to assay processing facilities for diagnostic processing.

FIG. 3A illustrates a data flow diagram 300A of using user devices 140 to provide remote health diagnostics with secure routing to assay processing facilities for diagnostic processing.

At 302, the user 111 may provide a biological sample to the assay device 110. For example, the user may prick a finger at the collection system 112.

At 304, the assay device 110 may collect the biological sample and perform the assay system 114. For example, puncture device such as micro-needles or nano-needles embedded in the collection system 112 of the assay device 110 may draw the biological sample to the assay system 114, which may perform one or more biological tests and convert the results in digital form on chip memory of the assay system 114 to produce the assay output.

At 306, the assay output may be transferred from the assay microchip to the user device 140 via an NFC query originated by user device 140. For example, the diagnostic agent 142 may initiate the NFC query and obtain the assay output from the assay device 110.

At 308A and 308B, the user device 140 may transmit a transaction to transfer the assay output, via the health data interchange server (illustrated in FIG. 3A as HDIS) 152, to a lab 160 for processing.

At 310, the lab 160 may analyze the assay output and generate a diagnostic result.

At 312A and 312B, the lab 160 may initiates a transaction to return the diagnostic result to the user device 140 via the health data interchange server 152.

At 314, the user device 140 may store the diagnostic result in a device memory of the user device 140.

At 316, the user may dispose the assay device 110 according to local instructions.

At 318, on a periodic basis, the health data interchange server 152 may perform anonymization and aggregation of testing and diagnostic results, and may generate aggregate reports for delivery to authorized constituents.

Figure 3B:
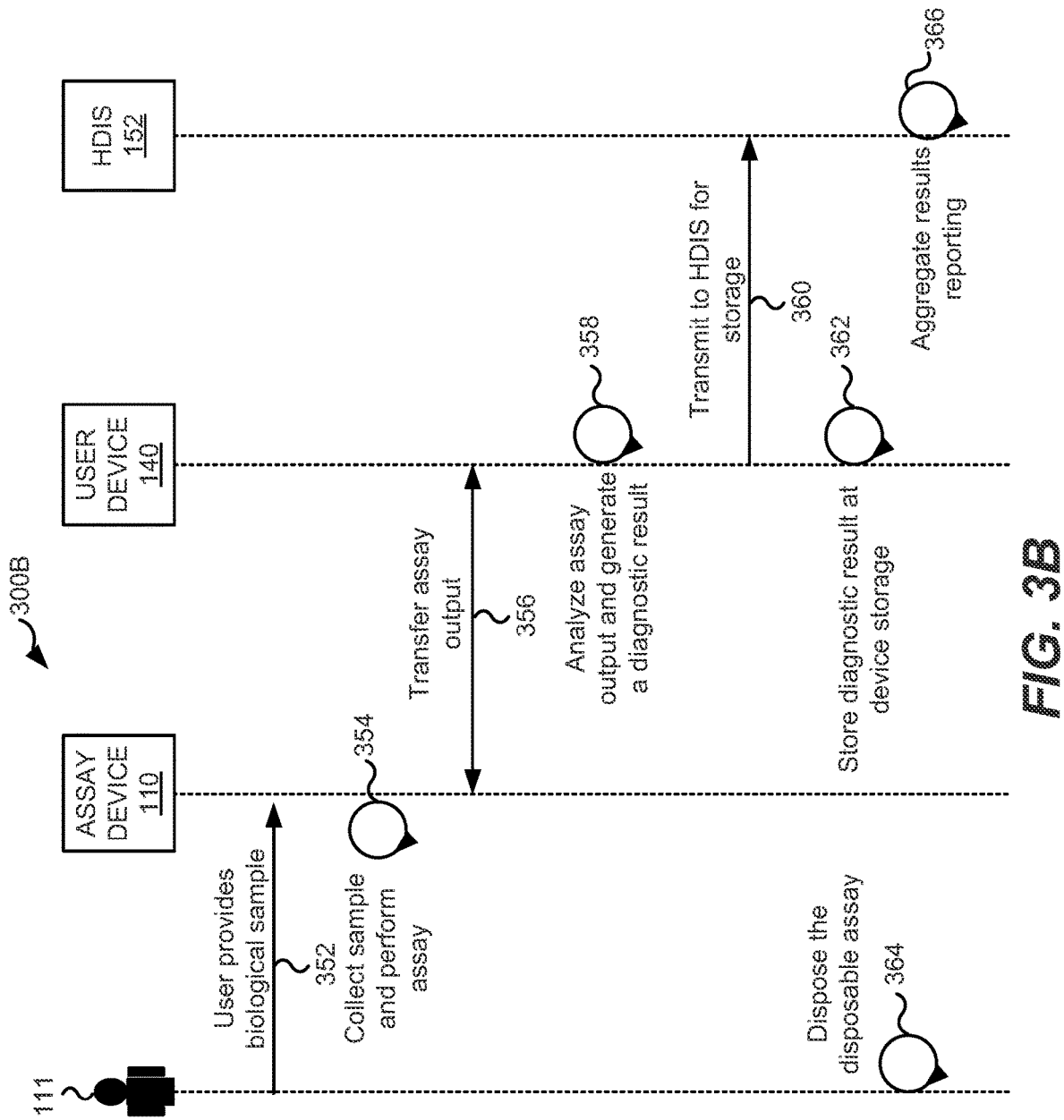
FIG. 3B illustrates a data flow diagram of using user devices to provide remote health data with diagnostic processing at the user devices.

FIG. 3B illustrates a data flow diagram 300B of using user devices 140 to provide remote health diagnostics with diagnostic processing at the user devices 140.

At 352, the user 111 may provide a biological sample to the assay device 110. For example, the user may prick a finger at the collection system 112.

At 354, the assay device 110 may collect the biological sample and perform the assay system 114. For example, puncture device such as micro-needles or nano-needles embedded in the collection system 112 of the assay device 110 may draw the biological sample to the assay system 114, which may perform one or more biological tests and convert the results in digital form on chip memory of the assay system 114 to produce the assay output.

At 356, the assay output may be transferred from the assay microchip to the user device 140 via an NFC query originated by user device 140. For example, the diagnostic agent 142 may initiate the NFC query and obtain the assay output from the assay device 110.

At 358, the user device 140 (as programmed by the diagnostic agent 142) may analyze the assay output and generate a diagnostic result.

At 360, the user device 140 may initiate a transaction to transmit the diagnostic result to the health data interchange server 152 for storage at the EMR database 159.

At 362, the user device 140 may store the diagnostic result in a device memory of the user device 140.

At 364, the user may dispose the assay device 110 according to local instructions.

At 366, on a periodic basis, the health data interchange server 152 may perform anonymization and aggregation of testing and diagnostic results, and may generate aggregate reports for delivery to authorized constituents.

Figure 4:
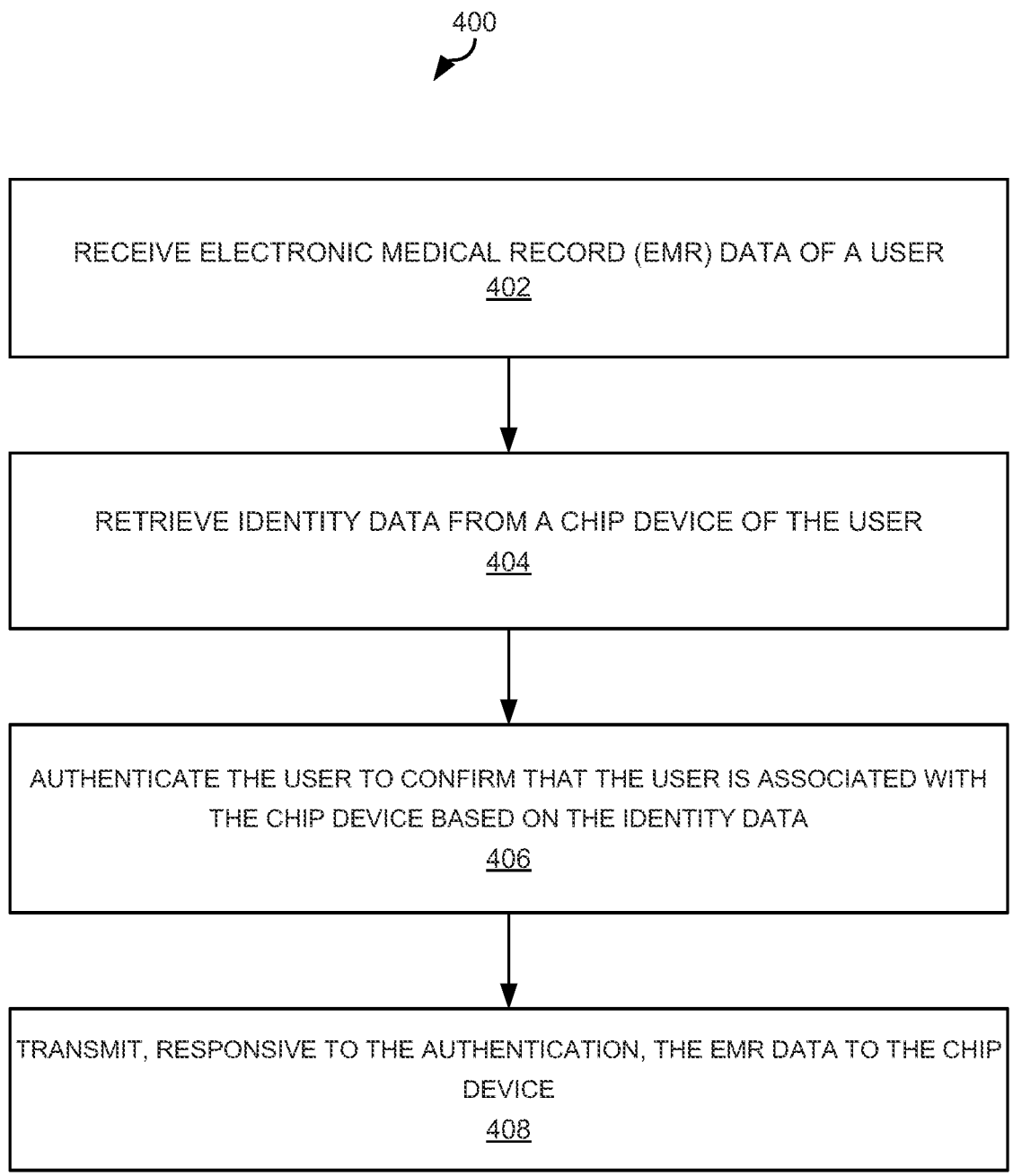
FIG. 4 illustrates a flow diagram of an example method of a POI device that processes health data.

FIG. 4 illustrates a flow diagram of an example method 400 of a POI device 130 that processes assay outputs from an assay device 110 configured as a LoC device.

At 402, the method 400 may include receiving EMR data of a user. In some examples, the EMR data may include an assay output from a LoC device (such as the assay device 110). The LoC device may have performed an assay on a biological sample. In this example, the assay output may be received via device-to-device communication such as via NFC, QR code, and/or other device-to-device technique. For example, receiving the assay output may include transmitting an NFC query to the LoC device. In these examples, the assay output may be transmitted by the LoC device responsive to the NFC query. In other examples, receiving the assay output may be via a QR code encoded and displayed by the LoC device. In some examples, the EMR data may be received from the health data interchange network 150 for storage at the chip device 120.

At 404, the method 400 may include retrieving identity data from a chip device, the chip device (such as chip device 120) of the user. In some examples, retrieving the identity data may include retrieving the identity data from the chip device via device-to-device communication. For example, the method 400 may include transmitting an NFC query to the chip device. In these examples, the identity data may be transmitted by the LoC device responsive to the NFC query.

At 406, the method 400 may include authenticating the user to confirm that the user is associated with the chip device based on the identity data. In some examples, the identity data may include a previously registered biometric hash (or other hashed identity information such as a PIN) of the user 111. In these examples, authenticating the user 111 may further include obtaining biometric identity data from the user. For example, the method 400 may include prompting the user 111 to input a fingerprint, other biometric, and/or other identity input. Upon receiving the input, the method 400 may include generating a biometric hash of the user 111 based on the biometric identity data and determining a match between the biometric hash and the previously registered biometric hash. The user may be authenticated based on the match.

At 408, the method 400 may include transmitting, responsive to the authentication, the EMR data to the chip device 120. For example, the method 400 may include transmitting the EMR data via a device-to-device communication, such as through an NFC write action to write the EMR data to the microchip 122 of the chip device 120.

Figure 5:
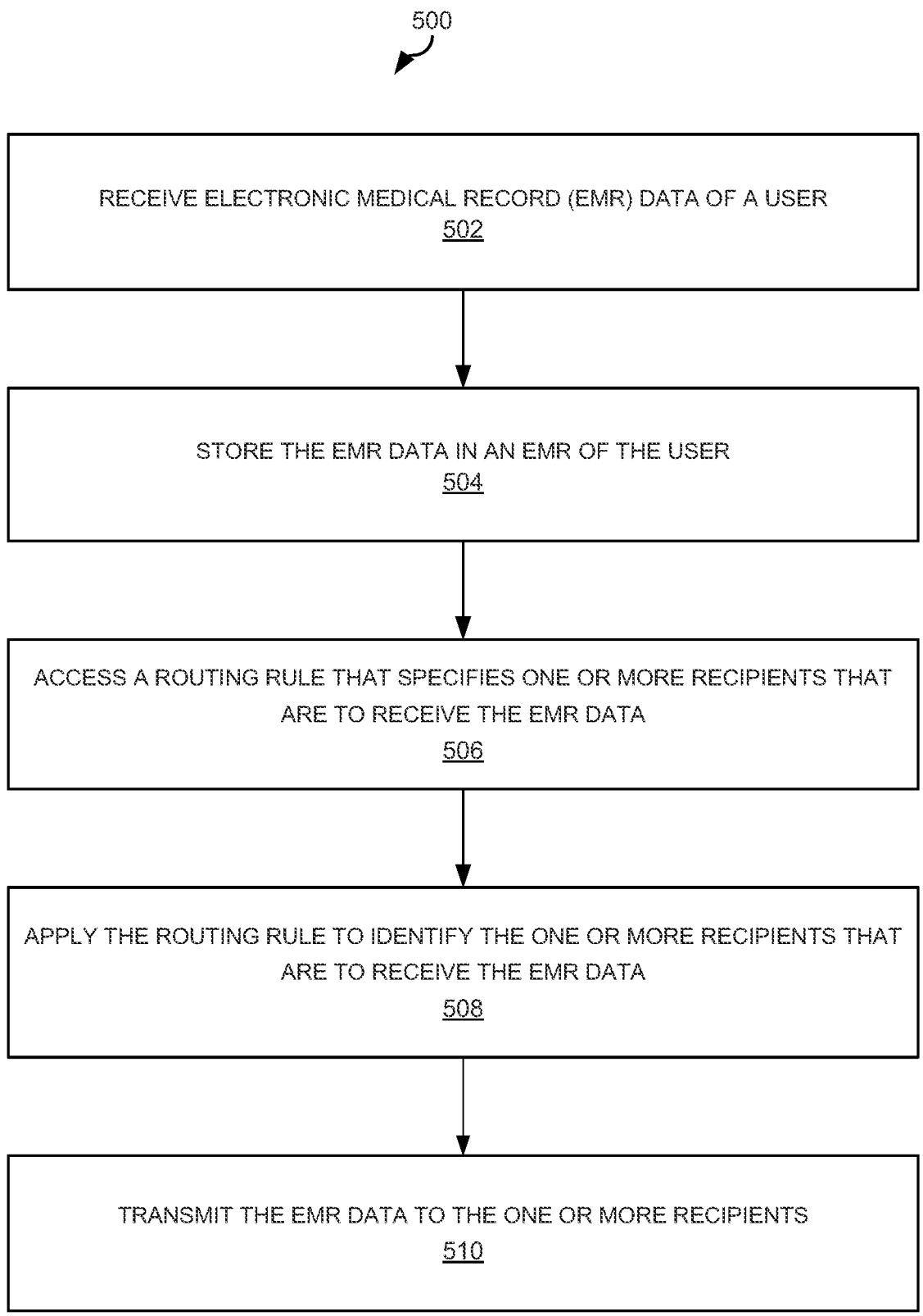
FIG. 5 illustrates a flow diagram of an example method of securely routing health data.

FIG. 5 illustrates a flow diagram of an example method 500 of securely routing health data. The method 500 may be implemented by the health data interchange server 152 illustrated in FIG. 1.

At 502, the method 500 may include receiving EMR data of a user. The EMR data may include data from an EMR system 180, data from a health data source 190, and/or a diagnostic result of an output of a LoC device, such as the assay device 110. In some examples, the method 500 may receiving the diagnostic result may include receiving an archive request, such as a transaction from a remote device (such as the POI device 130 or the user device 140) that includes the archive request. In these examples, the archive request may include the diagnostic result, which may have been generated at the remote device.

In other examples, receiving the diagnostic result may include receiving, from the remote device, a transaction that includes a request to route an assay output to a laboratory 160 for analysis. The method 500 further include generating a transaction identifier for the transaction, transmitting the assay output to the laboratory 160 with the transaction identifier, and receiving, from the laboratory, the diagnostic result. In these examples, the method 500 may further include routing the diagnostic result back to the remote device that transmitted the original transaction.

At 504, the method 500 may include storing the EMR data. For example, the diagnostic result may be stored in the EMR database 159.

At 506, the method 500 may include obtaining a routing rule (such as from routing rules database 157) that specifies recipients that are to receive the EMR data.

At 508, the method 500 may include applying the routing rule to identify one or more recipients that are to receive the EMR data.

At 510, the method 500 may include transmitting the diagnostic result to the one or more recipients. In some examples, the method 500 may include accessing a routing table database 153 to identify a respective network address of each of the one or more recipients. The routing table database 153 may store network address for each of the plurality of recipients.

Figure 6:
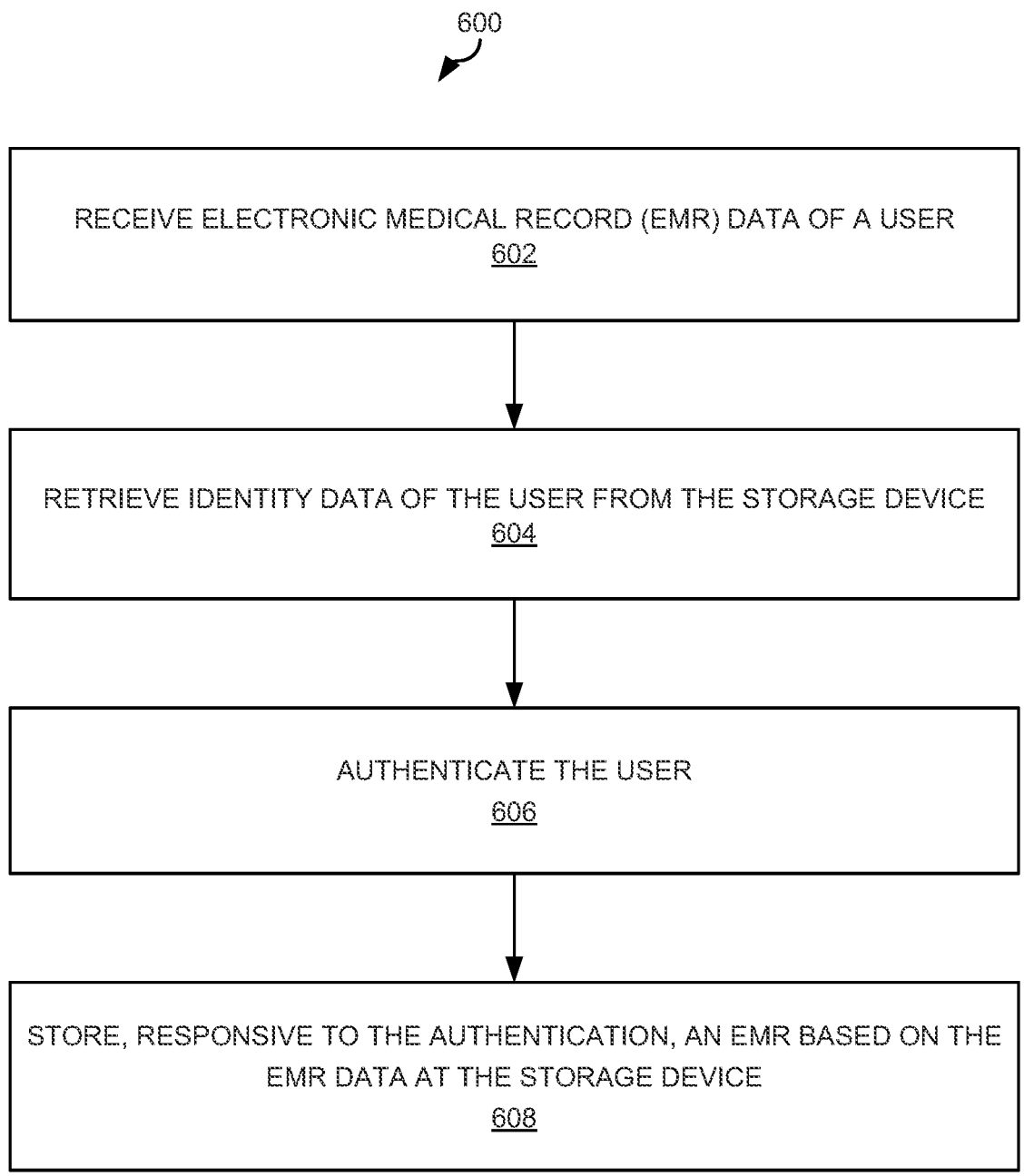
FIG. 6 illustrates a flow diagram of an example method of a user device that processes health data.

FIG. 6 illustrates a flow diagram of an example method 600 of a user device 140 that processes assay outputs from an assay device 110.

At 602, the method 600 may include receiving EMR data of a user an assay output from a LoC device (such as the assay device 110). The LoC device may have performed an assay on a biological sample.

At 604, the method 600 may include accessing a diagnostic result of the assay output. At 606, the method 600 may include retrieving identity data from the storage device, the user device 140 and the LoC device having been presented by a user for processing by the user device. At 608, the method 600 may include authenticating the user to confirm that the user based on the identity data. At 610, the method 600 may include storing, responsive to the authentication, the diagnostic result to the storage device.

It should be noted that the method 600 may be similar to the method 500 except that the method 600 may retrieve the identity data from an onboard memory and the diagnostic result may be stored on the onboard memory.

Figure 7:
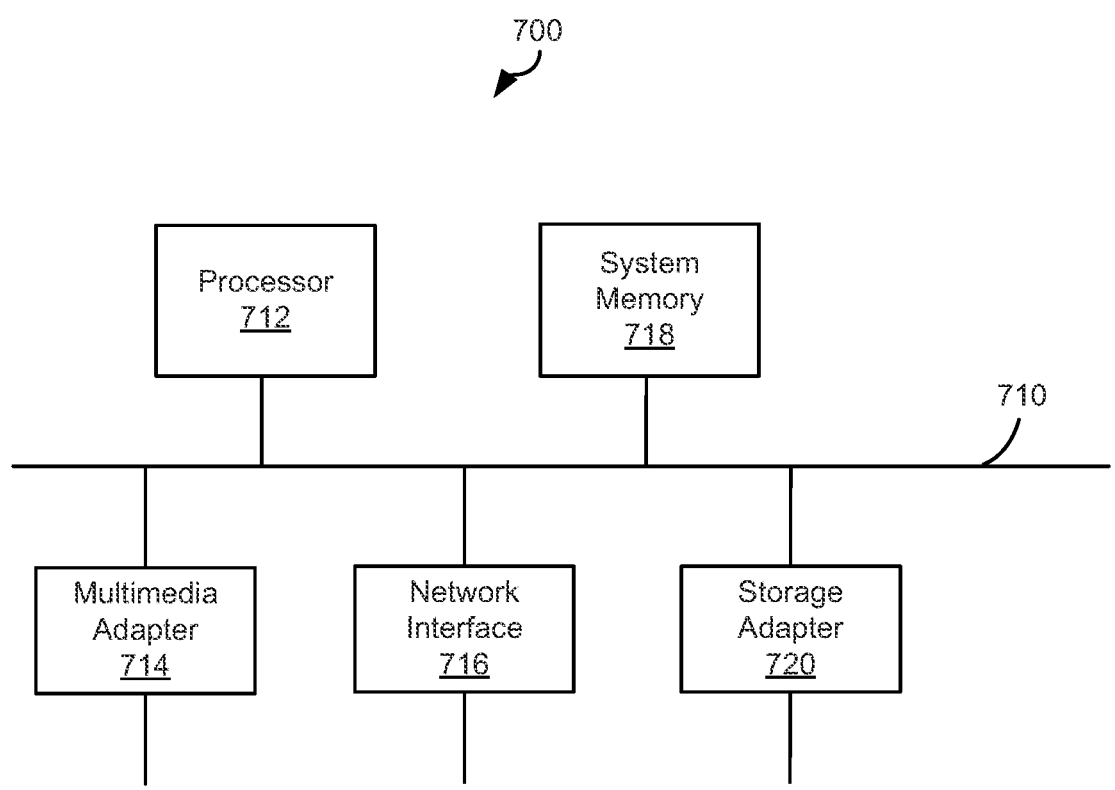
FIG. 7 illustrates an example of a computer system that may be implemented by devices illustrated in FIG. 1.

FIG. 7 illustrates an example of a computer system 700. The computer system 700 may be part of or include the system 100 to perform the functions and features described herein. For example, various ones of the devices of system 100 may be implemented based on some or all of the computer system 700. For example, the POI device 130, user device 140, devices of the labs 160A-N, devices of the constituents 170A-N, and the health data interchange server 152 may each implement some or all of the computer system 700.

The computer system 700 may include, among other things, an interconnect 710, a processor 712, a multimedia adapter 714, a network interface 716, a system memory 718, and a storage adapter 720.

The interconnect 710 may interconnect various subsystems, elements, and/or components of the computer system 700. As shown, the interconnect 710 may be an abstraction that may represent any one or more separate physical buses, point-to-point connections, or both, connected by appropriate bridges, adapters, or controllers. In some examples, the interconnect 710 may include a system bus, a peripheral component interconnect (PCI) bus or PCI-Express bus, a HyperTransport or industry standard architecture (ISA)) bus, a small computer system interface (SCSI) bus, a universal serial bus (USB), IIC (I2C) bus, or an Institute of Electrical and Electronics Engineers (IEEE) standard 1374 bus, or "firewire," or other similar interconnection element.

In some examples, the interconnect 710 may allow data communication between the processor 712 and system memory 718, which may include read-only memory (ROM) or flash memory (neither shown), and random-access memory (RAM) (not shown). It should be appreciated that the RAM may be the main memory into which an operating system and various application programs may be loaded. The ROM or flash memory may contain, among other code, the Basic Input-Output system (BIOS) which controls basic hardware operation such as the interaction with one or more peripheral components.

The processor 712 may control operations of the computer system 700. In some examples, the processor 712 may do so by executing instructions such as software or firmware stored in system memory 718 or other data via the storage adapter 720. In some examples, the processor 712 may be, or may include, one or more programmable general-purpose or special-purpose microprocessors, digital signal processors (DSPs), programmable controllers, application specific integrated circuits (ASICs), programmable logic device (PLDs), trust platform modules (TPMs), field-programmable gate arrays (FPGAs), other processing circuits, or a combination of these and other devices.

The multimedia adapter 714 may connect to various multimedia elements or peripherals. These may include devices associated with visual (e.g., video card or display), audio (e.g., sound card or speakers), and/or various input/output interfaces (e.g., mouse, keyboard, touchscreen).

The network interface 716 may provide the computer system 700 with an ability to communicate with a variety of remove devices over a network such as the communication network 107 illustrated in FIG. 1. The network interface 716 may include, for example, an Ethernet adapter, a Fibre Channel adapter, and/or other wired- or wireless-enabled adapter. The network interface 716 may provide a direct or indirect connection from one network element to another, and facilitate communication and between various network elements. The communication network 107 may therefore include a WAN (Wide Area Network), a SAN (Storage Area Network), a MAN (Metropolitan Area Network), a wireless network, a cellular communications network, a Public Switched Telephone Network, and/or other network through which system 100 components may communicate securely as described herein.

The storage adapter 720 may connect to a standard computer readable medium for storage and/or retrieval of information, such as a fixed disk drive (internal or external).

Other devices, components, elements, or subsystems (not illustrated) may be connected in a similar manner to the interconnect 710 or via a network such as the communication network 107. The devices and subsystems can be interconnected in different ways from that shown in FIG. 7. Instructions to implement various examples and implementations described herein may be stored in computer-readable storage media such as one or more of system memory 718 or other storage. Instructions to implement the present disclosure may also be received via one or more interfaces and stored in memory. The operating system provided on computer system 700 may be MS-DOS®, MS-WINDOWS®, OS/2®, OS X®, IOS®, ANDROID®, UNIX®, Linux®, or another operating system.

The account database 151, routing table database 153, transaction database 155, routing rules database 157, EMR database 159 or repositories described herein may be, include, or interface to, for example, an Oracle™ relational database sold commercially by Oracle Corporation. Other databases, such as Informix™, DB2 or other data storage, including file-based, or query formats, platforms, or resources such as OLAP (On Line Analytical Processing), SQL (Structured Query Language), a SAN (storage area network), Microsoft Access™ or others may also be used, incorporated, or accessed. The database may comprise one or more such databases that reside in one or more physical devices and in one or more physical locations. The database may include cloud-based storage solutions. The database may store a plurality of types of data and/or files and associated data or file descriptions, administrative information, or any other data. The various databases may store predefined and/or customized data described herein.

Throughout the disclosure, the terms "a" and "an" may be intended to denote at least one of a particular element. As used herein, the term "includes" means includes but not limited to, the term "including" means including but not limited to. The term "based on" means based at least in part on. In the Figures, the use of the letter "N" to denote plurality in reference symbols is not intended to refer to a particular number. For example, "160A-N" does not refer to 3 instances of 160, but rather "two or more."

The systems and processes are not limited to the specific embodiments described herein. In addition, components of each system and each process can be practiced independent and separate from other components and processes described herein. Each component and process also can be used in combination with other assembly packages and processes. The flow charts and descriptions thereof herein should not be understood to prescribe a fixed order of performing the method blocks described therein. Rather the method blocks may be performed in any order that is practicable including simultaneous performance of at least some method blocks. Furthermore, each of the methods may be performed by one or more of the system components illustrated in FIG. 1.

Having described aspects of the disclosure in detail, it will be apparent that modifications and variations are possible without departing from the scope of aspects of the disclosure as defined in the appended claims. As various changes could be made in the above constructions, products, and methods without departing from the scope of aspects of the disclosure, it is intended that all matter contained in the above description and shown in the accompanying drawings shall be interpreted as illustrative and not in a limiting sense.

While the disclosure has been described in terms of various specific embodiments, those skilled in the art will recognize that the disclosure can be practiced with modification within the spirit and scope of the claims.

As will be appreciated based on the foregoing specification, the above-described embodiments of the disclosure may be implemented using computer programming or engineering techniques including computer software, firmware, hardware or any combination or subset thereof. Any such resulting program, having computer-readable code means, may be embodied or provided within one or more computer-readable media, thereby making a computer program product, i.e., an article of manufacture, according to the discussed embodiments of the disclosure. Example computer-readable media may be, but are not limited to, a flash memory drive, digital versatile disc (DVD), compact disc (CD), fixed (hard) drive, diskette, optical disk, magnetic tape, semiconductor memory such as read-only memory (ROM), and/or any transmitting/receiving medium such as the Internet or other communication network or link. By way of example and not limitation, computer-readable media comprise computer-readable storage media and communication media. Computer-readable storage media are tangible and non-transitory and store information such as computer-readable instructions, data structures, program modules, and other data. Communication media, in contrast, typically embody computer-readable instructions, data structures, program modules, or other data in a transitory modulated signal such as a carrier wave or other transport mechanism and include any information delivery media. Combinations of any of the above are also included in the scope of computer-readable media. The article of manufacture containing the computer code may be made and/or used by executing the code directly from one medium, by copying the code from one medium to another medium, or by transmitting the code over a network.

This written description uses examples to disclose the embodiments, including the best mode, and also to enable any person skilled in the art to practice the embodiments, including making and using any devices or systems and performing any incorporated methods. The patentable scope of the disclosure is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A point of interaction (POI) device, comprising:
  a processor programmed to:
    access electronic medical record (EMR) data relating to a user, wherein the EMR data is tokenized or encrypted;
    transmit, to a health data interchange server, a request to route the tokenized or encrypted EMR data to a recipient, wherein the EMR data is routed based on one or more routing rules that specify one or more parameters that identify one or more recipients that can send or access the tokenized or encrypted EMR data over a network via the health data interchange server, wherein the one or more recipients are restricted to enrollees of the health data interchange server to improve routing security, wherein the routing rule comprises an assay-defined rule that defines send or access control based on a type of assay in the tokenized or encrypted EMR data, wherein results from a first type of assay that is included in the tokenized or encrypted EMR data are identified, and wherein the tokenized or encrypted EMR data is routed to the one or more recipients based on the first type of assay based on the routing rule;

retrieve identity data from a chip device of the user, wherein the identity data comprises a previously generated biometric hash of the user;

obtain biometric identity data from the user;

generate a biometric hash of the user based on the biometric identity data;

compare the biometric hash and the previously generated biometric hash retrieved from the chip device;

authenticate the user based on the comparison to confirm that the user is associated with the chip device based on the identity data; and transmit, responsive to the authentication, the EMR data to the chip device for storage at the chip device.

2. The POI device of claim 1, wherein to compare the biometric hash and the previously generated biometric hash retrieved from the chip device, th e processor is further programmed to:

determine a match between the biometric hash and the previously generated biometric hash, wherein the user is authenticated based on the match.

3. The POI device of claim 1, wherein the EMR data comprises a diagnostic result, and wherein the processor is further programmed to:

receive an assay output from a lab on chip (LoC) device, the LoC device having performed an assay on a biological sample of the user; and access the diagnostic result of the assay output.

4. The POI device of claim 3, wherein to receive the assay output, the processor is further programmed to transmit a Near-Field Communication (NFC) query to the LoC device, wherein the assay output is transmitted responsive to the NFC query.

5. The POI device of claim 3, wherein to receive the assay output, the processor is further programmed to receive the assay output via a digital health wallet of the POI device.

6. The POI device of claim 3, wherein to access the diagnostic result, the processor is further programmed to:

analyze the assay output to generate the diagnostic result.

7. The POI device of claim 5, wherein the processor is further programmed to:

transmit, to a health data interchange server via a communication network, a transaction comprising a request to archive the diagnostic result for aggregation with other diagnostic results of other users.

8. The POI device of claim 1, wherein the processor is further programmed to:

encode, based on a message format used by a payment network, a request to route an assay output to a laboratory that analyzes the assay output;

transmit, to a health data interchange server via a communication network, the encoded request;

receive, from the health data interchange server, a response to the routing request, the response including a diagnostic result of the assay output; and transmit the diagnostic result to the chip device for storage at the chip device.

9. The POI device of claim 1, wherein to retrieve the identity data, the processor is further programmed to transmit a Near-Field Communication (NFC) query to the chip device, wherein the identity data is transmitted responsive to the NFC query.

10. The POI device of claim 1, wherein to retrieve the identity data, the processor is further programmed to receive the identity data via a digital health wallet of the POI device.

11. The POI device of claim 1, wherein the EMR data comprises health data from a health data source, and wherein the processor is further programmed to receive the EMR data routed from a health interchange server.

12. A health data interchange server, comprising:

an Application Programming Interface (API) that tokenizes medical data prior to transport over a communication network;

a processor programmed to:

receive, via the API, electronic medical record (EMR) data associated with a user, the EMR data being received via an API that tokenizes the EMR data or as EMR data that has been encrypted based on a single-use advanced encryption standard key wrapped with a public key associated with the health data interchange server;

store the tokenized or encrypted EMR data in an EMR of the user;

access a routing rule that specifies one or more parameters that identify one or more recipients that can send or access the tokenized or encrypted EMR data over a network via the health data interchange server, wherein the one or more recipients are restricted to enrollees of the health data interchange server to improve routing security, wherein the routing rule comprises an assay-defined rule that defines send or access control based on a type of assay in the tokenized or encrypted EMR data;

identify results from a first type of assay that is included in the tokenized or encrypted EMIR data;

apply the routing rule to identify the one or more recipients that are to receive the tokenized or encrypted EMR data, wherein the one or more recipients are identified based on an enrolled network address for each of the one or more recipients; and transmit the tokenized or encrypted EMR data to the one or more recipients based on the enrolled network address for each of the one or more recipients, wherein the tokenized or encrypted EMR data is routed to the one or more recipients based on the first type of assay based on the routing rule.

13. The health data interchange server of claim 12, wherein to receive the EMR data, the processor is further programmed to:

receive an archive request from a remote device, the archive request comprising the EMR data.

14. The health data interchange server of claim 12, wherein to receive the EMR data, the processor is further programmed to:

receive a transaction from a remote device, the transaction encoded in a payment network message format and comprising the EMR data;

generate a transaction identifier for the transaction; and transmit the EMR data with the transaction identifier.

15. The health data interchange server of claim 12, wherein the EMR data comprises a diagnostic result, and wherein the processor is further programmed to:

receive an assay output of a lab on chip (LoC) device, the LoC device having performed an assay on a biological sample of the user; and receive a request to route the assay output to a laboratory for analysis;

receive, from the laboratory, the diagnostic result; and store the diagnostic result in an EMR of the user.

16. The health data interchange server of claim 12, wherein the routing rule further comprises the user-defined rule, and wherein the processor is further programmed to:

perform a lookup in a routing table to identify a network address of a recipient specified by the user-defined rule; and transmit the tokenized or encrypted EMR data to the network address.

17. A user device, comprising:

a storage device that stores identity data;

a processor programmed to:

receive, from a point of interaction (POI) device, a request for identity data, wherein the identity data comprises a previously generated biometric hash of a user;

retrieve identity data of the user from the storage device and transmit the identity data to the POI device for authentication, wherein the POI device generates a biometric hash based on biometric identity data of the user obtained at the POI device and compares the biometric hash and the previously generated biometric hash to authenticate the user;

receive electronic medical record (EMR) data from the POI device responsive to the user authentication; and store an EMR based on the EMR data at the storage device, wherein the EMR data is tokenized or encrypted and is to be routed based on one or more routing rules that specify one or more parameters that identify one or more recipients that can send or access the tokenized or encrypted EMR data over a network via a health data interchange server, wherein the one or more recipients are restricted to enrollees of the health data interchange server to improve routing security, wherein the routing rule comprises an assay-defined rule that defines send or access control based on a type of assay in the tokenized or encrypted EMR data, wherein results from a first type of assay that is included in the tokenized or encrypted EMR data are identified, and wherein the tokenized or encrypted EMR data is routed to the one or more recipients based on the first type of assay based on the routing rule.

18. The user device of claim 17, wherein the EMR data comprises a diagnostic result, and wherein the processor is further programmed to:

receive an assay output from a lab on chip (LoC) device, the LoC device having performed an assay on a biological sample of the user;

transmit the assay output to a health data interchange server that obtains the diagnostic result based on the assay output; and receive, from the health data interchange server, the diagnostic result.

19. The user device of claim 18, wherein to receive the assay output, the processor is further programmed to (i) transmit a Near-Field Communication (NFC) query to the LoC device, wherein the assay output is transmitted responsive to the NFC query, or (ii) receive the assay output via a digital health wallet of the user device.

* * * * *